(12) United States Patent
Lyders et al.

(10) Patent No.: US 11,237,133 B2
(45) Date of Patent: Feb. 1, 2022

(54) COMOLDED NON-DESTRUCTIVE INSPECTION STANDARD FUNCTIONING AS A BOND BUMP

(71) Applicant: United Technologies Corporation, Farmington, CT (US)

(72) Inventors: David R. Lyders, Glastonbury, CT (US); Andrew Pope, Glendale, NY (US); Christopher Avery, Malvern, PA (US); Daniel A. Rodrigues, Glastonbury, CT (US)

(73) Assignee: Raytheon Technologies Corporation, Farmington, CT (US)

( * ) Notice: Subject to any disclaimer, the term of this patent is extended or adjusted under 35 U.S.C. 154(b) by 134 days.

(21) Appl. No.: 16/690,639

(22) Filed: Nov. 21, 2019

(65) Prior Publication Data

US 2021/0156825 A1 May 27, 2021

(51) Int. Cl.
| | |
|---|---|
| *G01N 29/11* | (2006.01) |
| *G01N 29/30* | (2006.01) |
| *G01N 21/86* | (2006.01) |
| *G01N 23/083* | (2018.01) |
| *G01N 23/046* | (2018.01) |

(52) U.S. Cl.
CPC ............ *G01N 29/11* (2013.01); *G01N 29/30* (2013.01); *G01N 21/86* (2013.01); *G01N 23/046* (2013.01); *G01N 23/083* (2013.01); *G01N 2021/869* (2013.01)

(58) Field of Classification Search
CPC .. G01N 2223/646; G01N 29/11; G01N 29/30; G01N 23/083; G01N 21/86; G01N 23/046; G01N 2021/869
See application file for complete search history.

(56) References Cited

U.S. PATENT DOCUMENTS

| | | | |
|---|---|---|---|
| 7,736,452 B2 | 6/2010 | McBroom | |
| 8,215,181 B1 | 7/2012 | Helmink | |
| 9,103,758 B1 | 8/2015 | Frisch et al. | |
| 9,347,868 B2 | 5/2016 | Van Voast et al. | |
| 10,024,333 B2 | 7/2018 | Roach et al. | |
| 2010/0278440 A1* | 11/2010 | Dragovich | G06T 7/001 382/218 |
| 2015/0128709 A1* | 5/2015 | Stewart | G01N 29/045 73/588 |
| 2018/0297115 A1* | 10/2018 | Diwinsky | B33Y 50/02 |

* cited by examiner

*Primary Examiner* — Herbert K Roberts
*Assistant Examiner* — John M Royston
(74) *Attorney, Agent, or Firm* — Bachman & LaPointe, P.C.

(57) ABSTRACT

An inspection feature for an adhesive bond portion between parts of a component comprising the inspection feature extending from a surface of the part of the component a predetermined bond line thickness, the inspection feature having a density configured to imitate a defect of the adhesive bond portion responsive to a non-destructive inspection scan.

20 Claims, 1 Drawing Sheet

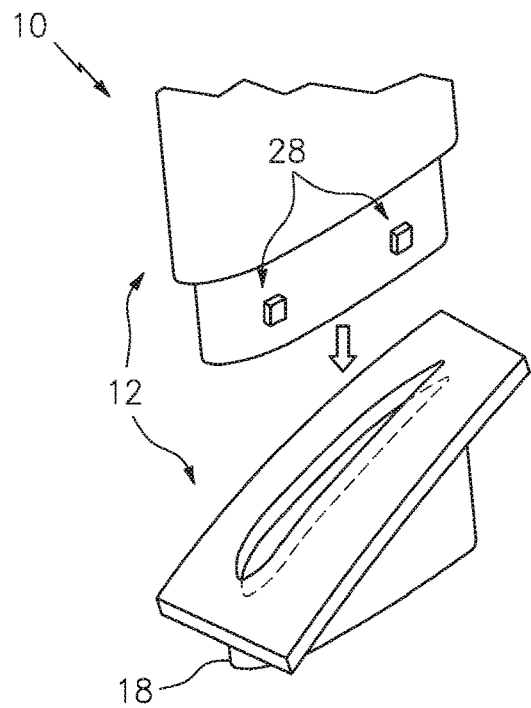
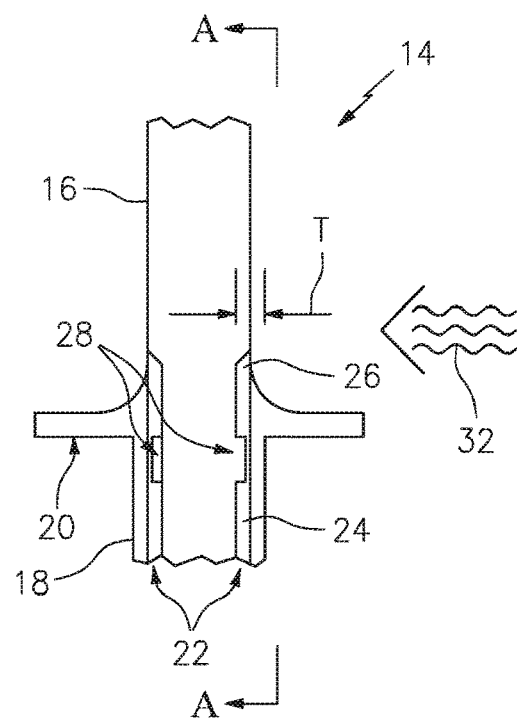
FIG. 1
FIG. 2
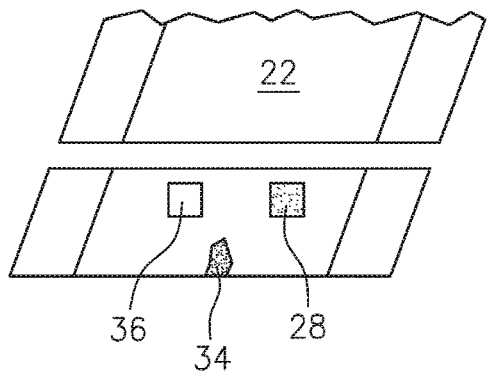
FIG. 5
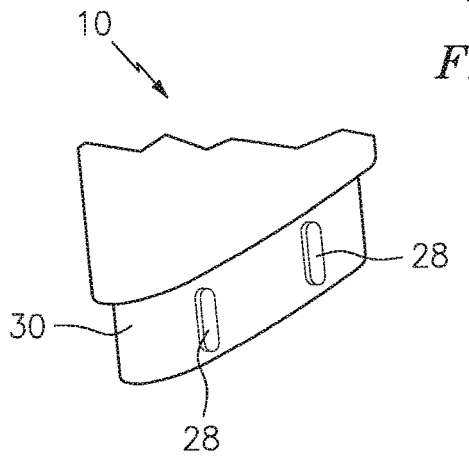
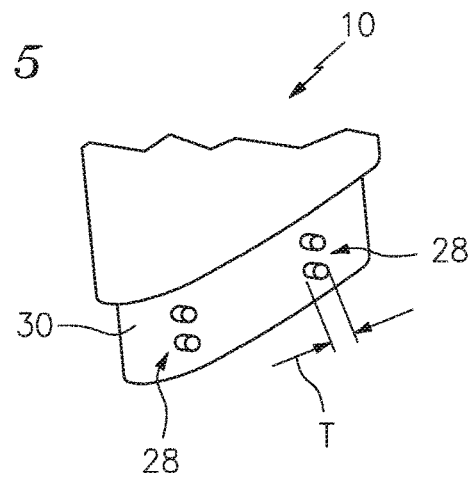
FIG. 3
FIG. 4

COMOLDED NON-DESTRUCTIVE INSPECTION STANDARD FUNCTIONING AS A BOND BUMP

BACKGROUND

The present disclosure is directed to the use of a modified bond bump for non-destructive examination.

When bonding two items together the adhesive used to bond the items includes a thickness, the adhesive includes a bond line. The thickness of the bond line needs to be controlled. Designs for bonding the two items together have used features to mechanically set the minimum thickness of the bond line. These features have been shaped as bond bumps or ridges that are machined or molded into one of the parts, or through the use of an adhesive with a scrim. If the bond is made at a structural location, the quality of the resulting bond line needs to be inspected, which can pose a challenge.

Ultrasonic Testing (UT), computerized axial tomography (CAT) Scan or X-Ray are just a few of the methods used to inspect the bond line. When utilizing these inspection techniques a threshold needs to be set in order to discern between actual voids in the bond and noise in the inspection data.

What is needed is a device that can be utilized to discern between actual voids and noise in the inspection data that also enables the proper bond line.

SUMMARY

In accordance with the present disclosure, there is provided an inspection feature for an adhesive bond portion between parts of a component comprising the inspection feature extending from a surface of the part of the component a predetermined bond line thickness, the inspection feature having a density configured to imitate a defect of the adhesive bond portion responsive to a non-destructive inspection scan.

In another and alternative embodiment, the inspection feature defines the predetermined bond line thickness which is a minimum thickness of the bond line.

In another and alternative embodiment, the inspection feature is co-molded with the part.

In another and alternative embodiment, the inspection feature is adhered to the surface of part.

In another and alternative embodiment, the inspection feature comprises a density such that the shade in a non-destructive inspection scan image of the inspection feature is similar in shade to the image of the defect.

In another and alternative embodiment, the inspection feature has a non-naturally occurring shape.

In another and alternative embodiment, the inspection feature comprises a density from about 0.0013 g/cm$^3$ to about 0.5 g/cm$^3$.

In accordance with the present disclosure, there is provided a component having parts bonded together by an adhesive bond portion comprising a first part attachable to a second part; a bond line thickness defined by the adhesive bond portion coupling the first part to the second part; an inspection feature extending a predetermined bond line thickness from a surface of at least one of the first part and the second part, the inspection feature having a density configured to imitate a defect of the adhesive bond portion responsive to a non-destructive inspection scan.

In another and alternative embodiment, the inspection feature is configured to produce an image produced from the non-destructive inspection scan having a shade that distinguishes from the shade of the adhesive bond portion.

In another and alternative embodiment, the inspection feature is configured to produce an image produced from the non-destructive inspection scan having a shade of the defect.

In another and alternative embodiment, the inspection feature is configured to produce an image from the non-destructive inspection scan having a non-naturally occurring shape.

In another and alternative embodiment, the defect comprises at least one of a void, gap, and crack.

In another and alternative embodiment, the inspection feature is configured to set a non-destructive examination standard configured to determine the defect being present in the adhesive bond portion.

In accordance with the present disclosure, there is provided a process for use of an inspection feature for an adhesive bond portion between parts of a component, the process comprising forming an inspection feature extending a predetermined bond line thickness from a surface of at least one of the first part and the second part, forming the adhesive bond portion coupling the first part to the second part to form the component; scanning the inspection feature and the adhesive bond portion with a non-destructive inspection scan; and creating an image from the non-destructive inspection scan, wherein the inspection feature comprises a density configured to imitate a defect within the adhesive bond portion responsive to the non-destructive inspection scan.

In another and alternative embodiment, the inspection feature is configured to set a non-destructive examination standard configured to determine the defect being present in the adhesive bond portion.

In another and alternative embodiment, the process further comprises producing the image of the inspection feature from the non-destructive inspection scan having a shade of the defect.

In another and alternative embodiment, the process further comprises producing an image of the inspection feature from the non-destructive inspection scan having a non-naturally occurring shape.

In another and alternative embodiment, the process further comprises setting a non-destructive examination standard utilizing the inspection feature, the standard configured to determine the defect being present in the adhesive bond portion.

In another and alternative embodiment, the process further comprises utilizing the non-destructive examination standard to form an image to compare with the image of the defect in the adhesive bond portion.

In another and alternative embodiment, the inspection feature defines the predetermined bond line thickness which is a minimum thickness of the bond line.

In another and alternative embodiment, the defect comprises at least one of a void, gap, and crack.

Other details of the modified bond bump for non-destructive examination are set forth in the following detailed description and the accompanying drawings wherein like reference numerals depict like elements.

BRIEF DESCRIPTION OF THE DRAWINGS

FIG. 1 is a schematic illustration of an exemplary component with inspection bond bump features prior to assembly.

FIG. 2 is a cross sectional schematic illustration of an exemplary component with inspection bond bump features after assembly.

FIG. 3 is a schematic illustration of an exemplary component with exemplary inspection bond bump feature.

FIG. 4 is a schematic illustration of an exemplary component with exemplary inspection bond bump feature.

FIG. 5 is a schematic illustration through cut line A at FIG. 2 of a non-destructive examination image of an exemplary component assembly with inspection bond bump feature.

DETAILED DESCRIPTION

Referring now to FIG. 1 and FIG. 2, there is illustrated a component 10, such as a vane. It is contemplated that the component 10 can be any variety of components that are assembled with separate parts 12 and bonded together to form a component assembly 14. The component 10 has an airfoil portion 16 with a base 18 having a platform portion 20. An adhesive 22 is utilized to couple the parts 12 together. The union of the parts 12 with the adhesive 22 creates a bond portion 24 between the parts 12. The bond portion 24 includes a predetermined thickness T along a bond line 26 of the bond portion 24. In order to set a minimum predetermined thickness T, an inspection surface feature, such as a bond bump or simply inspection feature 28 is employed. The minimum thickness T is a dimension that is at the lowest dimension necessary for an adequate bond of the adhesive 22 to attach the parts 12 together and meet the design requirements of the component 10.

Referring also to FIG. 3 and FIG. 4, the inspection feature 28 extends from the surface 30 of the component 10. The inspection feature 28 can be formed of most any shape that extends outwardly from the surface 30 and defines the thickness T, which is the minimum thickness of the bond line 26. The inspection feature 28 should be a shape that does not unnecessarily interfere with the proper bonding of the adhesive 22 allowing for proper contact and flow of the adhesive over the surface 30 as well as preventing void formation in the adhesive 22. In the exemplary embodiments, inspection feature 28 is shaped as a ridge shown at FIG. 3 and at FIG. 4 the inspection feature 28 is shaped as nubs. The inspection feature 28, can be formed by machining, molding or attaching elements to the surface 30 of the component.

FIG. 5 shows an illustration through cut line A at FIG. 2 of a non-destructive examination image of an exemplary component assembly with inspection feature 28. The adhesive 22 shown in the square sample 36, is revealed as unshaded. The square sample 36 indicates proper bonding. The inspection feature 28 is revealed in the image as having a shade that distinguishes from the adhesive being properly bonded at sample 36. The shade color in the image is similar in shade to the defect 34, which can be a void, or gap or other adhesive bonding defect.

In an exemplary embodiment the inspection feature 28 can be sized to ensure that non-destructive examination scanning beams 32 pass through the inspection feature 28 and indicate or reveal the presence of the inspection feature 28. During non-destructive examination, the scanning beams 32 pass through the part 12. The denser materials absorb more radiation, resulting in a lighter shade image. The areas of the part 12 or adhesive 22 that are incomplete, void or defect can show in the image as a darker shade than compared to the surrounding area. The inspection feature comprises a density such that the shade in a non-destructive inspection scan image of the inspection feature 28 is similar in shade to the image of the defect 34. The inspection feature 28 is configured to have a density that mimics the density of the defects 34, such as the density of an air bubble. The inspection feature 28 will reveal an image that has the same shade as a defect 34. The inspection feature 28 has a shape and size and density that is predetermined. In an exemplary embodiment, the inspection feature 28 can be a co-molded detail of a set size (such as, 0.25 inch×0.25 inch) to be used as a calibration standard for the inspection method being employed for the final bond line 26. The inspection feature 28 can be a material with a density closely resembling a void, pocket of air, crack or other defect. In an exemplary embodiment, the density of the inspection feature 28 can be from about 0.0013 $g/cm^3$ to about 0.5 $g/m^3$. In an exemplary embodiment, the inspection feature 28 can be less than 0.5 $g/m^3$. Exemplary materials of the inspection feature 28 can include aerogel, balsa, aerated closed cell plastic or polymer. The inspection feature 28 can be formed integrally with the part 12. In an exemplary embodiment, the inspection feature 28 can be applied to the surface 30 or otherwise attached to the surface 30 of the part 12. A peel and stick attachable inspection feature 28 is contemplated. The inspection feature 28 can be modified and adapted to optimize the type of non-destructive inspection and type of materials utilized in the part 12 and adhesive 22. The inspection feature 28 can be a non-naturally occurring shape, such as triangle, square and the like to be better identified as a standard and discerned from an actual defect 34.

Thus, utilizing the inspection feature 28, a standard can be created that an inspector can utilize to compare with actual defects 34 in the bond line 26. The inspection feature 28 can be configured to set a non-destructive examination standard that can be relied upon to determine if defects 34 are present in the bond 24. The inspection feature 28 can serve as a "fly away" calibration standard, enabling the non-destructive inspection method to dial in, calibrate, the inspection settings to correctly size the inspection feature 28 and thus be calibrated to accurately size any bond line defects 34.

A technical advantage of the disclosed inspection feature includes simplified machining of the part to be bonded, as the inspection feature can be co-molded or applied after formation of the part.

Another technical advantage of the disclosed inspection feature includes the inspection feature becoming a non-destructive inspection standard set and sized to function as a calibration standard for a variety of non-destructive inspection, such as (UT, CT Scan, X-Ray and the like).

Another technical advantage of the disclosed inspection feature includes a height that can set the thickness of the bond line.

Another technical advantage is that the disclosed inspection feature can function as a bond bump.

Another technical advantage of the disclosed inspection feature includes optimization of the inspection feature to direct injected adhesive and minimize void formation.

There has been provided a modified bond bump for non-destructive examination. While the modified bond bump for non-destructive examination has been described in the context of specific embodiments thereof, other unforeseen alternatives, modifications, and variations may become apparent to those skilled in the art having read the foregoing description. Accordingly, it is intended to embrace those alternatives, modifications, and variations which fall within the broad scope of the appended claims.

What is claimed is:

1. An inspection feature for an adhesive bond portion between parts of a component comprising:

said inspection feature extending from a surface of the part of the component a predetermined bond line thickness, said inspection feature having a density configured to imitate a defect of the adhesive bond portion responsive to a non-destructive inspection scan.

2. The inspection feature for an adhesive bond portion between parts of a component according to claim 1, wherein said inspection feature defines the predetermined bond line thickness which is a minimum thickness of the bond line.

3. The inspection feature for an adhesive bond portion between parts of a component according to claim 1, wherein said inspection feature is co-molded with the part.

4. The inspection feature for an adhesive bond portion between parts of a component according to claim 1, wherein said inspection feature is adhered to the surface of the part.

5. The inspection feature for an adhesive bond portion between parts of a component according to claim 1, wherein said inspection feature comprises a density such that the shade in a non-destructive inspection scan image of the inspection feature is similar in shade to the image of the defect.

6. The inspection feature for an adhesive bond portion between parts of a component according to claim 1, wherein said inspection feature has a non-naturally occurring shape.

7. The inspection feature for an adhesive bond portion between parts of a component according to claim 1, wherein said inspection feature comprises a density from about 0.0013 $g/cm^3$ to about 0.5 $g/cm^3$.

8. A component having parts bonded together by an adhesive bond portion comprising:
a first part attachable to a second part;
a bond line thickness defined by the adhesive bond portion coupling said first part to said second part;
an inspection feature extending a predetermined bond line thickness from a surface of at least one of the first part and the second part, said inspection feature having a density configured to imitate a defect of the adhesive bond portion responsive to a non-destructive inspection scan.

9. The component having parts bonded together by an adhesive bond portion according to claim 8, wherein said inspection feature is configured to produce an image produced from the non-destructive inspection scan having a shade that distinguishes from the shade of the adhesive bond portion.

10. The component having parts bonded together by an adhesive bond portion according to claim 8, wherein said inspection feature is configured to produce an image produced from the non-destructive inspection scan having a shade of the defect.

11. The component having parts bonded together by an adhesive bond portion according to claim 8, wherein said inspection feature is configured to produce an image from the non-destructive inspection scan having a non-naturally occurring shape.

12. The component having parts bonded together by an adhesive bond portion according to claim 8, wherein said defect comprises at least one of a void, gap, and crack.

13. The component having parts bonded together by an adhesive bond portion according to claim 8, wherein said inspection feature is configured to set a non-destructive examination standard configured to determine said defect being present in the adhesive bond portion.

14. A process for use of an inspection feature for an adhesive bond portion between a first part and a second part of a component comprising:
forming an inspection feature extending a predetermined bond line thickness from a surface of at least one of the first part and the second part,
forming the adhesive bond portion coupling said first part to said second part to form the component;
scanning said inspection feature and said adhesive bond portion with a non-destructive inspection scan; and
creating an image from the non-destructive inspection scan, wherein said inspection feature comprises a density configured to imitate a defect within the adhesive bond portion responsive to the non-destructive inspection scan.

15. The process of claim 14, further comprising:
producing the image of the inspection feature from the non-destructive inspection scan having a shade of the defect.

16. The process of claim 14, further comprising:
producing an image of the inspection feature from the non-destructive inspection scan having a non-naturally occurring shape.

17. The process of claim 14, further comprising:
setting a non-destructive examination standard utilizing the inspection feature, said standard configured to determine the defect being present in the adhesive bond portion.

18. The process of claim 17, further comprising
utilizing said non-destructive examination standard to form an image to compare with the image of the defect in the adhesive bond portion.

19. The process of claim 14, wherein said inspection feature defines the predetermined bond line thickness which is a minimum thickness of the bond line.

20. The process of claim 14, wherein said defect comprises at least one of a void, gap, and crack.

* * * * *